United States Patent [19]

Allred, III et al.

[11] Patent Number: 5,345,925
[45] Date of Patent: Sep. 13, 1994

[54] SELF-ADVANCING ENDOSCOPE

[75] Inventors: Jimmie B. Allred, III; Peter Bettis, both of Skaneateles; Karl Decerce, Liverpool, all of N.Y.

[73] Assignee: Welch Allyn, Inc., Skaneateles Falls, N.Y.

[21] Appl. No.: 37,937

[22] Filed: Mar. 26, 1993

[51] Int. Cl.⁵ ............................................. A61B 1/00
[52] U.S. Cl. .......................................... 128/4; 128/6
[58] Field of Search ................. 128/4, 6; 604/95, 96, 604/156; 227/179; 175/51, 76; 186/17; 73/866.5, 623; 606/171

[56] References Cited

U.S. PATENT DOCUMENTS

| | | | |
|---|---|---|---|
| 4,589,414 | 5/1986 | Yoshida et al. | 606/171 |
| 4,700,693 | 10/1987 | Lia et al. | |
| 4,838,859 | 6/1989 | Strassmann | 604/95 |
| 4,934,786 | 6/1990 | Krauter | |
| 5,243,967 | 9/1993 | Hibino | 128/6 |

Primary Examiner—Richard J. Apley
Assistant Examiner—John P. Leubecker
Attorney, Agent, or Firm—Harris Beach & Wilcox

[57] ABSTRACT

There is provided a propulsion unit that is incorporated in an endoscope or borescope. Advancement of the insertion tube through a passageway is attained by a series of washers or similar members that can be mounted on the insertion tube of the borescope and can independently move coaxially with respect to the insertion tube. When the tube is passed into a passageway, the washers contact the walls. A drive motor that is associated with the insertion tube axially reciprocates the washers and transmits the axial motion to the insertion tube. The rate of movement of the washers is nonuniform and washer movements are phased such that at any point in time more washers are moving in one direction than in the opposite direction. The resultant frictional forces are such that net forward motion of the tube is achieved.

15 Claims, 6 Drawing Sheets

SELF-ADVANCING ENDOSCOPE

BACKGROUND OF THE INVENTION

1. Field of the Invention

This invention relates to a propelling mechanism in an intracavity viewing instrument such as an endoscope or a borescope that is adapted to urge the instrument along a narrow and tortuous passage.

2. Description of the Prior Art

Endoscopes are extremely useful in the medical arts for inspecting the interior of certain organs that are otherwise inaccessible to a physician's examination. Hollow viscera, such as the gastrointestinal tract often are required to be inspected for the presence of pathological conditions and diseases. In the physiological state these organs are comprised of long tortuous passageways having flexures and valves that admit of great difficulty in negotiation, even by skilled operators. The splenic and hepatic flexures of the colon and the ileocecal valve are examples of obstacles that can frustrate a medical examination of the bowel. Furthermore friction between the lining of the organ and the instrument limits the distance that the endoscope can be inserted without risking perforation of the organ or damage to the tissues. When these organs become diseased they can be focally or diffusely narrowed. They may also become kinked and structurally weakened so that the passage of the endoscope becomes even more difficult and the risk of perforation and serious injury to the patient increases.

In industrial applications borescopes are highly useful in inspecting the condition of otherwise inaccessible passages, such as the insides of boiler tubes, or hydraulic lines in a turbine or jet engine. These passages also tend to be tortuous. Consequently, because of twists and turns in the passageway, and because of friction between the sides of the insertion tube and the walls of the passageway, the distance into the passageway that the borescope insertion tube can be pushed or pulled is oftentimes limited.

It would be advantageous to provide means on the borescope or endoscope to permit it to advance itself through tortuous passages such as the intestine or curved pipes. Such means would ideally:

(a) produce an axial thrust distributed along the insertion tube to avoid buckling, stretching, or excessive localized insertion tube-wall friction;

(b) be controllable from the proximal end of the insertion tube;

(c) be simple, reliable, and inexpensive to manufacture and maintain;

(d) not substantially increase the diameter of the insertion tube of the borescope;

(e) be capable of operation when only a part of the insertion tube is inserted into the passageway to be inspected;

(f) be applicable to existing borescopes or endoscopes, either permanently or as a removable option; and (g) be insensitive to the diameter of the passageway in which the borescope or endoscope tube is utilized.

U.S. Pat. No. 4,934,786 to Krauter, having a common assignee herewith, addresses the above problem. In Krauter there is shown an arrangement whereby a pair of elongated bladders is wrapped helically over the insertion tube, configured such that one bladder of the pair expands radially and distally, while the other bladder expands radially and proximally. Compressed air or another fluid is provided periodically to the two bladders such that they are inflated in alternate phase relationship to move the insertion tube in a desired proximal or distal direction. However this arrangement requires a control mechanism to properly phase the supply of fluid to the bladders, and, since there are only two bladders, the motion achieved by alternately inflating the bladders fails to adequately propel the probe under some conditions.

SUMMARY OF THE INVENTION

It is therefore a primary object of the present invention to provide a flexible insertion tube for a borescope, endoscope, or other similar instrument with means for advancing or withdrawing the insertion tube within an elongated, narrow, and tortuous passageway, and which avoids the drawbacks of the prior art.

It is another object of the invention to provide such a device which is relatively simple and inexpensive, reliable, and which does not significantly increase the profile of the insertion tube:

These and other objects of the present invention are attained by a propulsion unit that is incorporated in an endoscope or borescope. Advancement of the insertion tube through a passageway is attained by a series of washers or similar members that can be mounted on the insertion tube of the borescope and can independently move coaxially with respect to the insertion tube. When the tube is passed into a passageway, the washers contact the walls. A drive motor that is associated with the insertion tube axially reciprocates the washers and transmits the axial motion to the insertion tube. Because there is substantial friction between the washers and the walls of the passageway, the washers do not readily slip on the walls as they reciprocate. Consequently the insertion tube is forced into relative movement with the walls.

Figure 1:
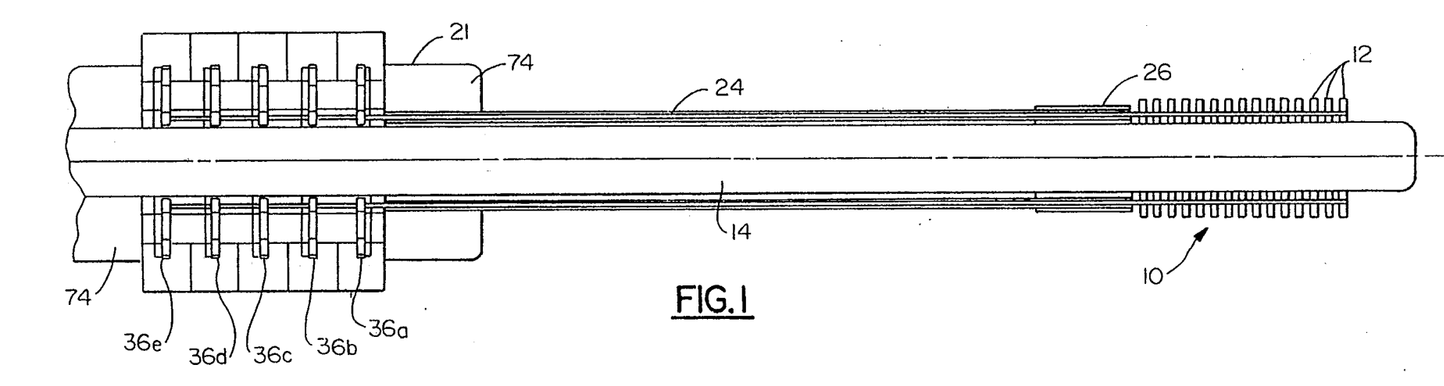
FIG. 1 is a sectional view of a borescope having a propulsion unit constructed in accordance with the present invention.

It should be apparent that if the washers uniformly reciprocated on the axis of the insertion tube, counteracting forces imparted by movements in opposite directions would cancel and there would be no net progression of the insertion tube in a desired direction. However in accordance with the present invention, the rate of movement of the washers is nonuniform and washer movements are phased such that at any point in time more washers are moving in one direction than in the opposite direction. This necessarily implies that a majority of washers are moving relatively slowly in a given direction, while a minority are moving more rapidly in the opposite direction. The frictional forces exerted by the minority against the passage walls are ineffective to counter the opposing frictional forces on the passageway that are imparted by the majority, and the minority washers therefore slide against the wall of the passageway while the majority hold firm thereon. As a result there is net motion of the insertion tube relative to the wall of the passageway and the insertion tube advances. It is evident from the foregoing that a minimum of three washers is required; however, as shown in FIG. 1, a practical embodiment requires a larger number of washers.

Figure 4:
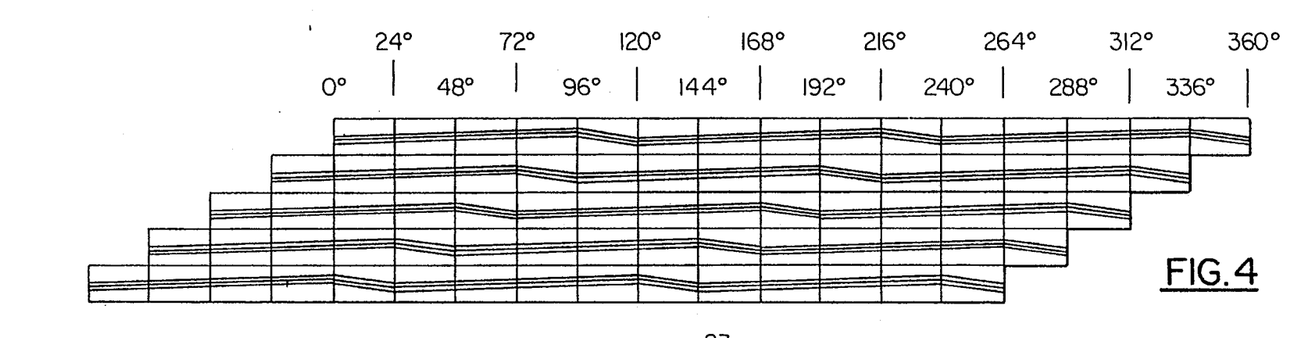
FIG. 4 is a timing chart for the washers in the propulsion unit of FIG. 1.

In the preferred embodiment a periodic cycle is established within an array of a given number of washers. The cyclic motion of each of the washers in the array is out of phase by a predetermined value with that of the succeeding washer. For each washer a portion of the cycle determined by the reciprocal of the number of washers is allocated to one direction of motion, and the remainder of the cycle to the opposite direction. Reference may be had to FIG. 4 wherein the phasing of a unit of five washers is shown. It is evident that each washer slowly moves in one direction for 4/5 of the period and returns to a starting position during the remaining 1/5 of the period, and that each washer differs in phase by a value of 24°, that is (120°/5), with the succeeding washer. Expressed in another way, at any point in time 4 washers are moving along the axis of the insertion tube in one direction at an average rate R and the fifth washer is moving in the opposite direction at an average rate 4R. An observer of the device in operation perceives a periodic motion wave that is produced by changes in the spacing between washers as each washer moves in one direction and then returns to a starting position, much like the apparent wave produced by the legs of a centipede as it crawls along the ground.

The optimum number of washers in a wave varies with the application. Short waves involve fewer mechanical parts, and often result in faster motion, while a long wave is conducive to better traction and smoother action, but may present control problems.

In a motion cycle phasing can be established whereby the trailing washer in the propulsion unit is the first to move in a forward direction. Successive leading washers then execute forward motions in turn. This produces a wave which appears to an observer to progress in the same direction as the rapid washer motion. Such a wave is herein termed a "compression wave". Alternatively the washers can be phased so that the leading washer is the first in the cycle to execute a forward motion, followed in turn by each successively trailing washer. This arrangement produces a wave which appears to an observer to move opposite the direction of rapid washer motion, and is termed an "expansion wave". For medical applications, an expansion wave is preferred.

BRIEF DESCRIPTION OF THE DRAWINGS

For a better understanding of these and other objects of the present invention, reference is made to the detailed description of the invention which is to be read in conjunction with the following drawings, wherein.

DESCRIPTION OF THE PREFERRED EMBODIMENT

Turning now to the drawings, and in particular to FIG. 1, there is shown a preferred embodiment of the invention, wherein a propulsion unit, shown generally at 10, is employed in conjunction with a typical viewing instrument such as a borescope or an endoscope.

Figure 10:
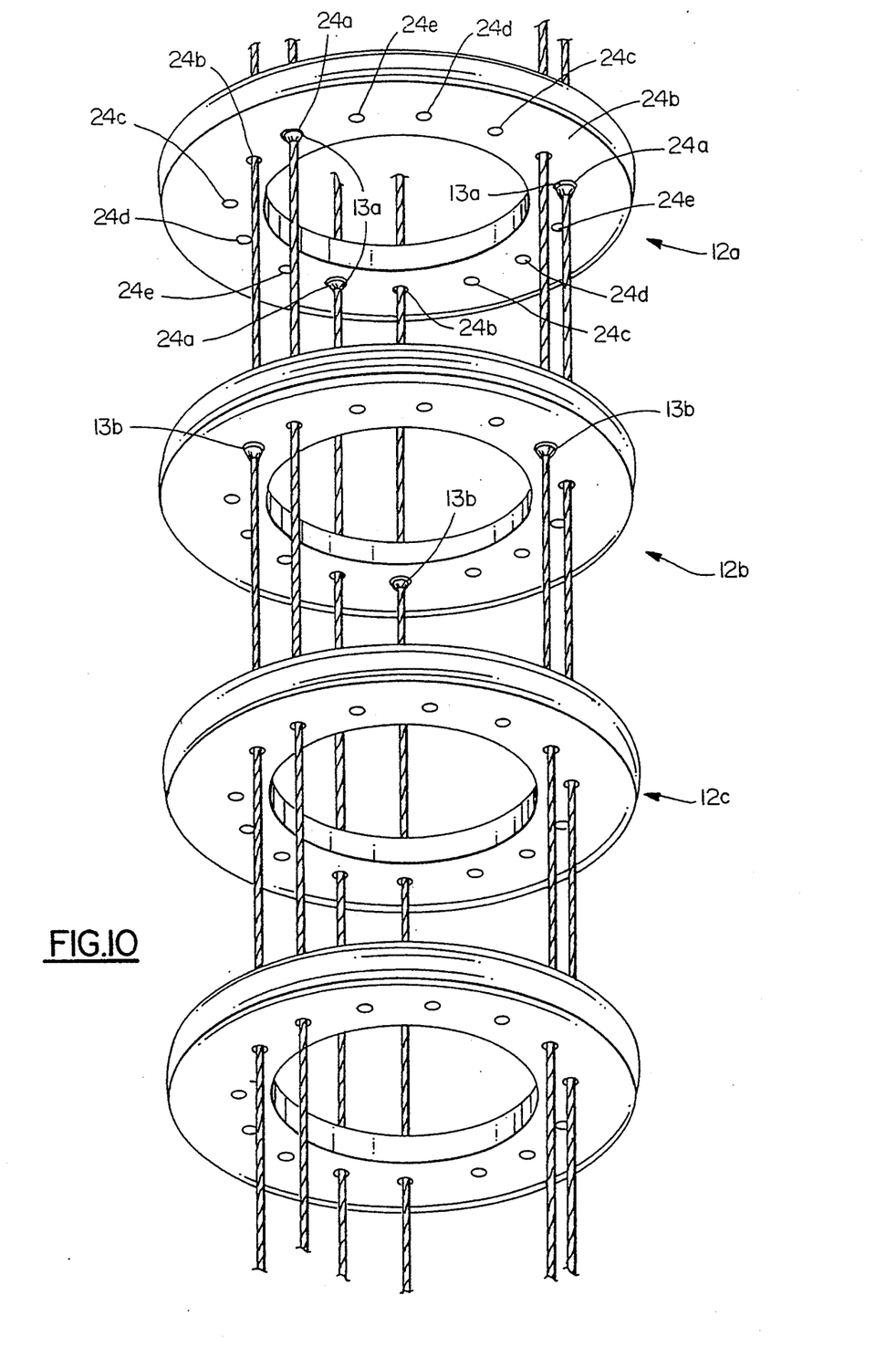
FIG. 10 is a detailed perspective view of two propulsive washers in the assembly of FIG. 1A and their respective drive cables.

The propulsion unit is mounted on the insertion tube 14 of the borescope or endoscope and consists of a plurality of axially aligned washers 12 that surround the insertion tube 14. The washers 12 can independently slide along the long axis of insertion tube 14. While in the preferred embodiment the washers are arranged in three sets of five washers each, other mechanical arrangements are possible without departing from the spirit of the invention, and the configuration of the washers or similar members can vary to achieve optimal traction in a given application. The sliding motion of washers 12 is actuated by rigid rods or cables 24. Referring to FIG. 10, there are shown adjacent washers 12a–12c, each having a plurality of small peripheral holes bored therethrough. Fifteen drive cables, indicated as three repeating sequences 24a–24e (some omitted for clarity) pass through the holes, and every fifth cable 24a is bonded to washer 12a at point 13a by an adhesive or the like. The remaining cables 24b–24e freely pass through the holes and are slidable on washer 12a. The cables continue through washer 12b, cables 24b being bonded to washer 12b at points 13b, and so on. As will be explained in further detail below, every fifth cable, such as 24a, 24a, 24a, moves reciprocally and in phase. It will now be evident that each of the washers is controlled by three drive cables, each bonded to the washer and equally spaced apart along its circumference, moving together in phase to cause the washer to reciprocate axially, and at the same time retaining the washer 12 in orthogonal alignment with the insertion tube 14. Furthermore there is a predetermined phase difference in the cyclic motions of cables 24a and the other cables 24b–24e, so that adjacent washers such as 12a, 12b also move out of phase with one another.

Figure 1A:
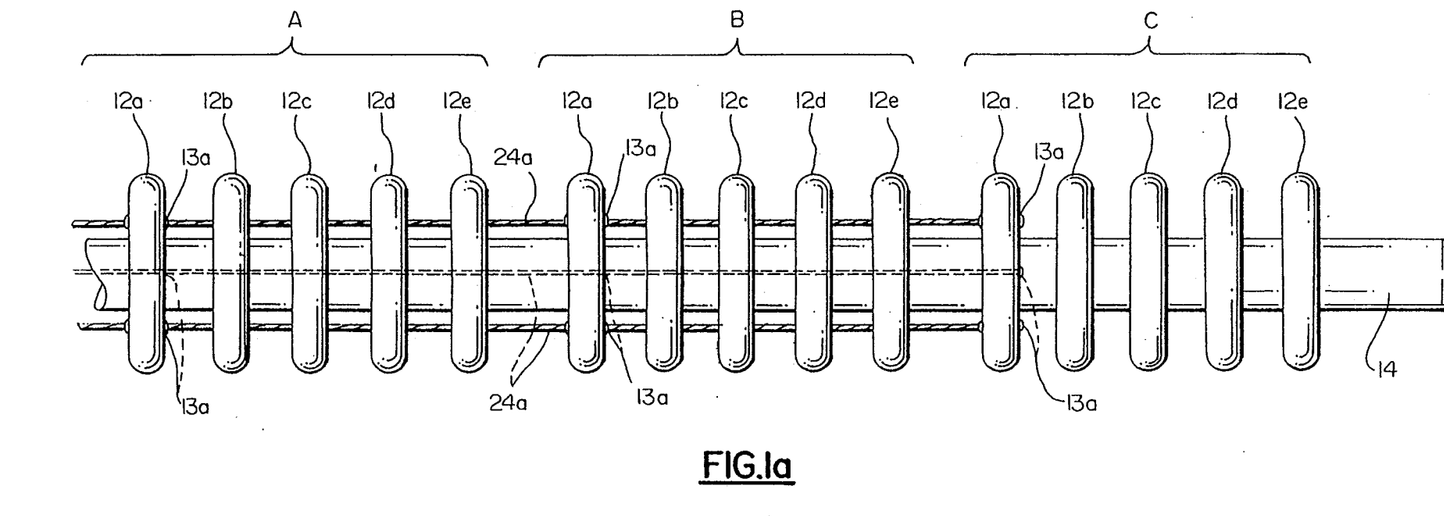
FIG. 1a is an enlarged partial elevation of the distal portion of the borescope shown in FIG. 1.
Figure 2:
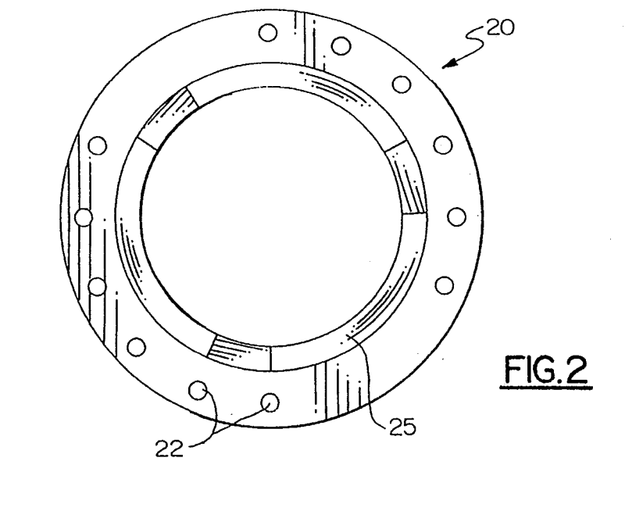
FIG. 2 is a plan view of a cam that is a component of the propulsion unit of FIG. 1.

The coordinated motion of the washers 12 can be further understood with reference to FIG. 1a. Here the washers 12 are grouped into three groups A-C, each group including five cables 12a–12e. For washers 12a, the connections with drive cables 24a are shown. The remaining drive cables 24b–24e are omitted for clarity of illustration. Group C is unique, in that the cables terminate on the washers to which they are bonded. For example Cables 24a terminate in washer 12a, rather than continuing therethrough as in groups A and B. As each washer 12a is bonded to three cables 24a, it will be apparent that cables 24a control three washers that move in phase with the motion of cables 24a. The driving mechanism for the cables is arranged such that the phase difference between any washers 12a and 12b is constant. It is important that each washer be controlled by at least three drive cables to maintain orthogonal alignment with the tube 14.

Figure 3:
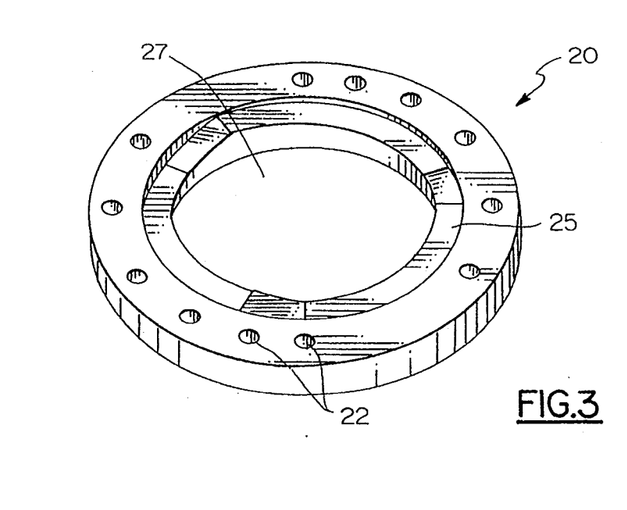
FIG. 3 is an enlarged perspective view of the cam of FIG. 2 which has been exaggerated for purposes of illustration.
Figures 5, 5A, 6:
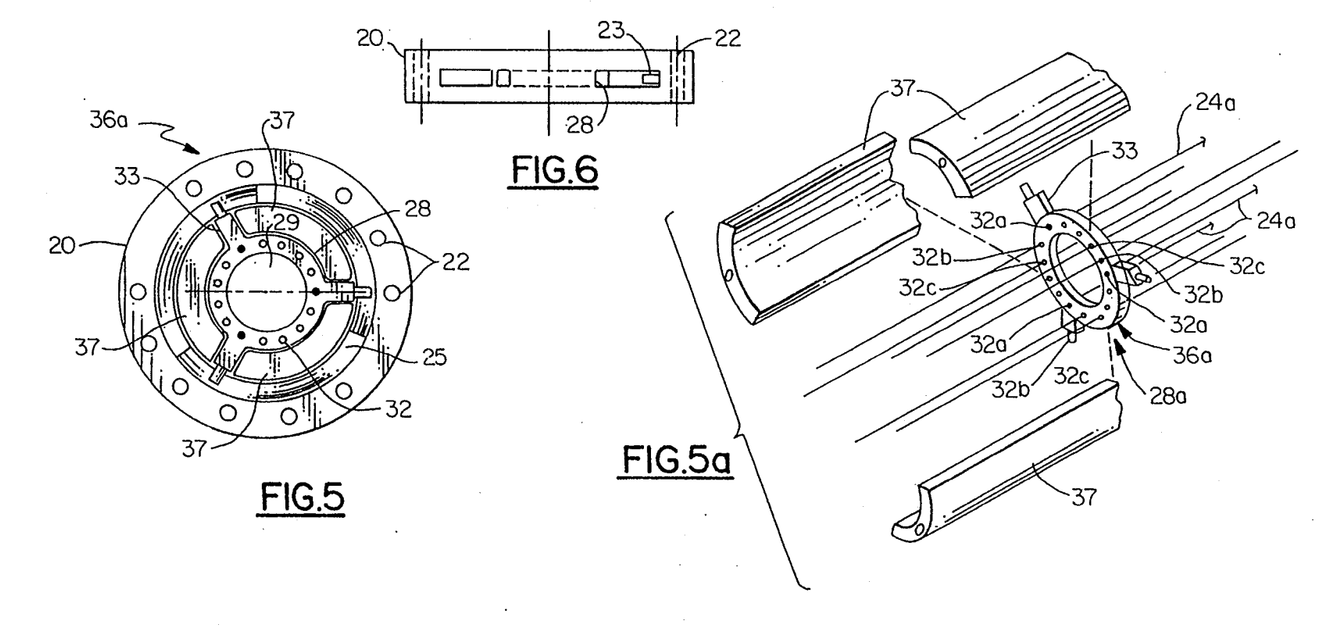
FIG. 5 is a partial sectional view of a cam and cam follower that are components of the propulsion unit of FIG. 1.
FIG. 5a is a partial exploded view of the driver assembly of the borescope of FIG. 1.
FIG. 6 is a top elevation of a cam and cam follower combination that comprises a subassembly of the propulsion unit of FIG. 1.

Turning now to FIGS. 3–5 there is shown a member 20 of a mated pair of cams. A plurality of bores 22 are drilled through the peripheral portion of the washer to receive pins or dowels (not shown) for purposes of alignment and to relate each mated pair of cams to an adjacent mated pair by an appropriate phase difference.

Figure 7:
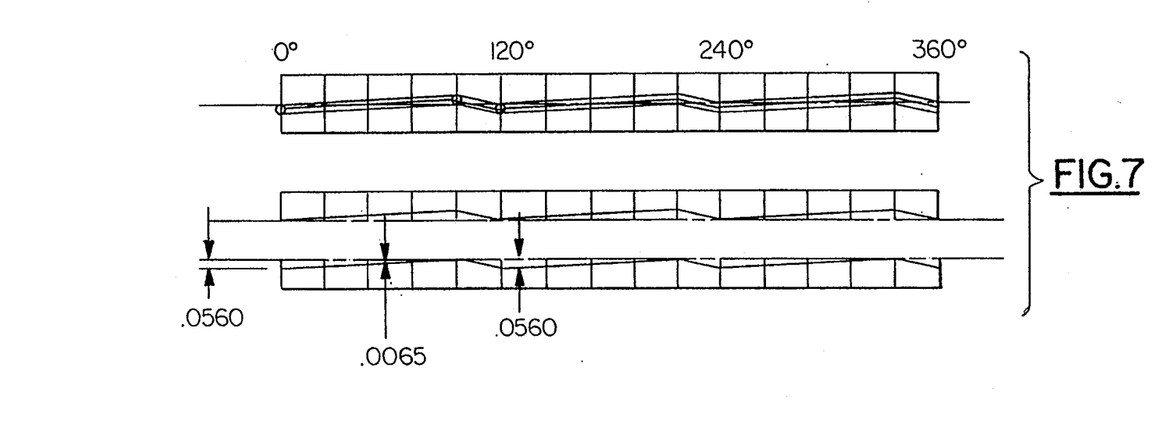
FIG. 7 is a chart that is helpful in understanding the construction of the components of FIG. 5.

A circular groove or channel 25 is machined on a face of one member of cam 20 adjacent its central passage 27. The floor of the groove 25 forms the profile of the cam. When two members are mated to form a cam unit 36, the grooves face one another to define a recess 23 that communicates with central passage 27 and accepts cam follower 28. It is preferable that the circumference of the cam 20 be subdivided into three identical profiles, each covering a sector of 120°. A chart of an exemplary profile of the cam 20 is depicted in FIG. 7.

Cam follower 28 is shown in FIGS. 5 and 5a. It is an axially aligned disk or washer having a central aperture 29. The diameter of the disk is smaller than the diameter of the central passage 27 of washer 20, so that the cam follower nests within the central passage 27. Radial projections 33 extend from the disk into recess 23 and ride on surfaces of the grooves 25 that form the profiles of the cam, and central aperture 29 surrounds insertion tube 14. In the preferred embodiment, there are five cam units 36 in drive unit 21, each comprising cam follower 28 and two enclosing members 20. Cam follower 28 has fifteen peripheral apertures or bores 32, that carry drive cables 24. In FIG. 5a a particular cam follower 28a is illustrated in a partial exploded view. The enclosing members 20 and most of the drive cables 24 are omitted for clarity. Every fifth drive cable 24a is bonded to cam follower 28 at a point 34a by adhesive, solder, or any suitable means and terminates thereon. The remaining drive cables pass through their respective bores and are freely slidable therethrough. The members 20 enclosing cam followers 28a, 28b are rotatable with respect to insertion tube 14, while the cam followers are restrained from rotating about tube 14 by crescent-shaped longitudinal guides 37 which pass through all the cam units 36a 36e (FIG. 1). Guides 37 are disposed within passage 27 (FIG. 5) and are nested around the cam followers 28, bearing on radial projections 33 as members 20 rotate about cam followers 28. The guides 37 are anchored by pins or dowels (not shown) to collars 74, 74 (see FIG. 1). The collars are disposed on either side of drive unit 21, and are fixed to insertion tube 14 by well known methods such as press fitting, adhesive or set screws. When the members 20 are rotated by the drive unit 21, cam followers 28 and the drive cables 24 are forced into phased reciprocating axial motion, but are restrained from rotating by guides 37. This is reflected in the motion of washers 12 in accordance with the cam profiles.

Other constructions of the cam and cam follower combination are possible to achieve reciprocating axial motion of the washers. For example the cams could be external to the washers, so that pairing would not be required. After the cam and cam follower had moved the washers in a desired first longitudinal direction spring loading or other tensioning of the washers could accomplish reciprocation in a second longitudinal direction.

In FIG. 4 there is shown a timing chart for the case where there are 5 washers in the propulsion unit, the cam follower has 3 radial projections, each riding on an identical profile so that three axial motion cycles are completed during a 360° revolution of a cam member 20. Each axial motion cycle of a washer thus requires 120° of rotatory motion. 96° (4/5 of 120°) are correspond to the rise of the cam profile, while the fall requires the remaining 24° (1/5 of 120°). It can also be seen that the cycles of succeeding washers are 24° out of phase. The motions of the washers in the embodiment of the invention that is depicted in FIG. 4 are phased to produce an expansion wave.

It can now be appreciated that when the cam units 36 are rotated, either manually or by a drive motor, drive cables 24 will be forced by the axial motion of cam followers 28 to reciprocate along the longitudinal axis of insertion tube 14, thereby moving the washers 12 back and forth along the axis.

It is possible to construct the propulsion unit so that the washers or similar members are arranged in N groups, each group having a given number M of washers, so that there is a total of M×N washers. For example in the above described example with reference to FIG. 4, there could be an integral multiple 5N washers divided into N groups of 5, the correspondingly ranked washers in each group moving in phase. The washers within a given group move in accordance with the timing relationships shown in FIG. 4.

In operation the borescope is placed so that propulsion unit 10 is in contact with the wall of a passageway to be negotiated and the drive actuated. Friction between the washers 12 and the wall of the passageway results in a net movement of the insertion tube in a longitudinal direction as the washers 12 reciprocate in accordance with the timing chart of FIG. 4. The direction of rotation of cam units 36 may be reversed to achieve retrograde motion of the instrument.

Figure 8:
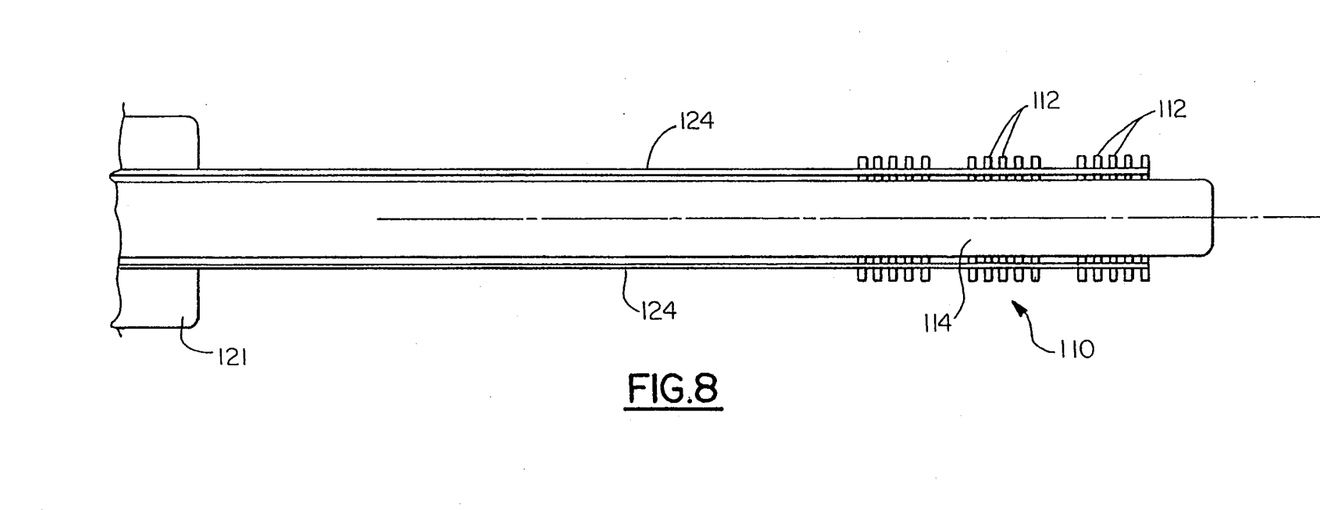
FIG. 8 is a partially schematic sectional view of a first alternate embodiment of the invention.

Referring now to FIG. 8 there is shown a first alternate embodiment of the invention that features a plurality of propulsion units 110. The units may share drive cables 124 which run to respective cam followers. In difficult applications the multiple propulsion units 110 provide increased traction and simplify the advancement of the instrument.

Figure 9:
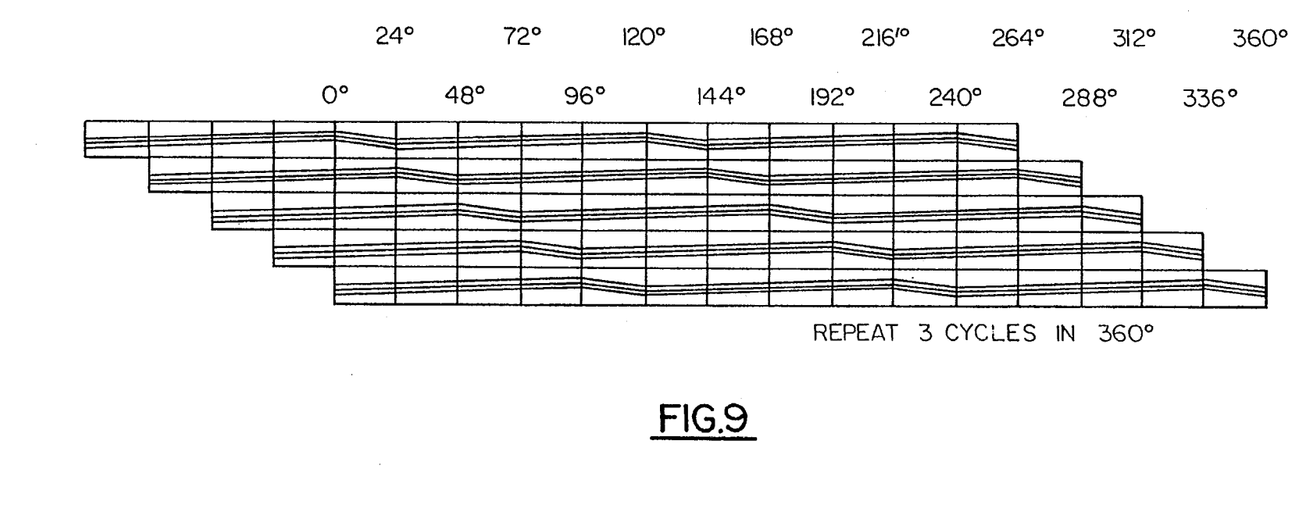
FIG. 9 is a timing chart for the washers in the propulsion unit of a second alternate embodiment of the invention.

In a second alternate embodiment of the invention, the washers in the device of FIG. 1 may be arranged so that their phased reciprocal axial motions produce a compression wave. The motions of the washers in such an arrangement are shown in FIG. 9.

While this invention has been explained with reference to the structure disclosed herein, it is not confined to the details set forth and this application is intended to cover any modifications and changes as may come within the scope of the following claims.

What is claimed is:

1. A self-advancing intracavity viewing instrument including:
   an elongated insertion tube having a longitudinal axis, and;
   a propulsion unit connected to said insertion tube comprising: at least three axially aligned washers disposed on said insertion tube and being independently slidable thereon, said washers projecting radially beyond said insertion tube whereby said washers can contact the walls of a passageway; and
   means associated with said washers for imparting nonuniform reciprocating axial motion to said washers such that at any point in time more washers are moving in one direction than in an opposite direction;
   whereby said insertion tube is propelled along a passageway when said washers are in contact with the walls of a passageway and are in reciprocating axial motion.

2. The instrument of claim 1 wherein said washers are divided into a plurality of groups, each group having a given number of washers, the reciprocating axial motion of each member being in phase with the motion of a respectively ranked member of another group, whereby the groups cooperate to propel said insertion tube.

3. The instrument of claim 1 wherein the nonuniform reciprocating axial motion is phased to produce an expansion wave.

4. The instrument of claim 1 wherein the nonuniform reciprocating axial motion is phased to produce a compression wave.

5. A self-advancing intracavity viewing instrument including:
   an elongated insertion tube having a longitudinal axis; and
   a propulsion unit connected to said insertion tube comprising:
      at least three axially aligned washers including a leading washer and a trailing washer disposed on said insertion tube and being independently slidable thereon, said washers projecting radially beyond said insertion tube whereby said washers can contact the walls of a passageway; and
      at least three cams and at least three cam follower means associated with said cams, said cam follower means being operatively connected with said washers for imparting nonuniform reciprocating axial motion to said washers such that at any point in time more washers are moving in one direction than in an opposite direction;
      drive means for revolving said cams about the longitudinal axis of the insertion tube;
      means for restraining said cam follower means from rotating about said insertion tube when said cams are being revolved;
      whereby said insertion tube is propelled when said washers are in contact with the walls of a passageway and are in reciprocating axial motion.

6. The instrument of claim 5 wherein said washers are divided into a plurality of groups, each group having a given number of washers, the reciprocating axial motion of each member being in phase with the motion of a respectively ranked member of another group, whereby the groups cooperate to propel said insertion tube.

7. The instrument of claim 5 wherein said cam and cam followers are arranged so that said leading washer is the first of said washers to execute a forward motion.

8. The instrument of claim 5 wherein said cam and cam followers are arranged so that said trailing washer is the first of said washers to execute a forward motion.

9. A self-advancing intracavity viewing instrument comprising:
   an elongated insertion tue having a longitudinal axis;
   at least three cams each comprising paired members in face-to-face contact, said cams being rotatable about said longitudinal axis and disposed in a fixed longitudinal position with respect to aid longitudinal axis;
   at least three cam followers each disposed between one of said paired members in engagement with a profile formed by said paired members, said cam followers being movable along said longitudinal axis and fixed from rotation thereabout;
   at least three axially reciprocating washers including a leading washer and a trailing washer, each washer being slidably mounted on said insertion tube, for propelling said insertion tube along a passageway when said reciprocating washers are in contact with a wall of said passageway;
   at least three rigid cables connected to said reciprocating washers and to said cam followers; and
   drive means for revolving said cams about the longitudinal axis of said insertion tube, said cams and cam followers imparting nonuniform reciprocating axial motion to said washers along the axis of said insertion tube such that at any point in time more washers are moving in one direction than in an opposite direction.

10. The instrument of claim 9, wherein each washer has an axial reciprocating motion that differs in phase by a predetermined magnitude from the motion of another washer.

11. The instrument of claim 10, wherein said reciprocating washers comprise a plurality of groups of washers, each group comprising an equal number of washer, each washer of a group being in phase with a respectively ranked member of another group, whereby the groups cooperate to propel said insertion tube.

12. The instrument of claim 10, wherein said group comprises five washers.

13. The instrument of claim 11, wherein said reciprocating washers comprise three groups, each group having five washers.

14. The instrument of claim 10 wherein said cam and cam follower are arranged so that said leading washer is the first of said washers to execute a forward motion.

15. The instrument of claim 10 wherein said cam and cam followers are arranged so that said trailing washer is the first of said washers to execute a forward motion.

* * * * *